(12) United States Patent
Divi et al.

(10) Patent No.: US 8,455,692 B2
(45) Date of Patent: Jun. 4, 2013

(54) PROCESS FOR RESOLUTION OF 1-(3-HYDROXYPHENYL)-2-METHYLAMINO ETHANOL

(75) Inventors: Murali Krishna Prasad Divi, Hyderabad (IN); Padakandla Gundu Rao, Hyderabad (IN); Bolneni Nageswara Rao, Hyderabad (IN); Medepudi Ramesh Babu, Hyderabad (IN); Mutyala Krishnaji Rao, Hyderabad (IN); Allupati Padmanav Patro, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 164 days.

(21) Appl. No.: 12/976,257

(22) Filed: Dec. 22, 2010

(65) Prior Publication Data
US 2012/0108848 A1    May 3, 2012

(30) Foreign Application Priority Data

Nov. 1, 2010 (IN) .......................... 3258/CHE/2010

(51) Int. Cl.
*C07C 215/00* (2006.01)
*C07C 211/00* (2006.01)

(52) U.S. Cl.
USPC .......................................... 564/355; 564/336

(58) Field of Classification Search
None
See application file for complete search history.

(56) References Cited

U.S. PATENT DOCUMENTS

| 1,932,347 A | 10/1933 | Legerlotz et al. |
| 3,825,583 A | 7/1974 | Hussain et al. |
| 4,028,368 A | 6/1977 | Bodor et al. |
| 4,158,005 A | 6/1979 | Bodor et al. |
| 6,187,956 B1 | 2/2001 | Klinger et al. |
| 6,670,476 B2 * | 12/2003 | Harms .......................... 544/349 |

FOREIGN PATENT DOCUMENTS

| DE | 543529 | 2/1932 |
| DE | 585164 | 9/1933 |
| IN | 221620 | 6/2001 |
| WO | 2008077560 A1 | 7/2008 |
| WO | 2009086283 A1 | 7/2009 |
| WO | 2010031776 A2 | 3/2010 |

OTHER PUBLICATIONS

IN-216663 Derwent abstract 2008, p. 1-2.*
Pavia et al . "Introduction to Organic Laboratory Techniques a Microscale Approach", 1990, pp. 228 and 632-633.*
Hisashi Takahashi, et al. Practical Asymmetric synthesis of (R)-(–)-Phenylephrine Hydrochloride Catalyzed by (2R,4R)-MCCPM-Rhodium Complex, Tetrahedron Letters 1989, 30, 367-370.
S.I. Sergievskaya, et al. The Synthesis of m-Amino(Hydroxy)-Phenyl-8-Methylamino-Ethanol and the Catalytic Reduction of m-Nitroacetophenone, J. Gen. Chem, USSR, 22, 1952-559-563.
Mukund K. Gurjar, et al., A Practical Synthesis of (R)-(–)Phenylephrine Hydrochloride, Organic Process Research & Development 1998, 422-424, Indian Institute of Chemical Technology, Hyderabad 500 007, India, and C P consulting, Inc., 241 Walnut Street, Wellesley, Massachusetts 02481.

* cited by examiner

*Primary Examiner* — Clinton Brooks
(74) *Attorney, Agent, or Firm* — Caesar, Rivise, Bernstein, Cohen & Pokotilow, Ltd.

(57) ABSTRACT

Resolution of the title compound to its active isomer (R)-1-(3-hydroxyphenyl)-2-methylamino ethanol with (R)-naproxen as a resolving agent.

11 Claims, No Drawings

PROCESS FOR RESOLUTION OF 1-(3-HYDROXYPHENYL)-2-METHYLAMINO ETHANOL

CROSS-REFERENCE TO RELATED APPLICATIONS

This application claims priority from India Application Serial No. 3258/CHE/2010, filed on Nov. 1, 2010, entitled Process for Resolution of 1-(3-HYDROXYPHENYL)-2-METHYLAMINO ETHANOL, which application is assigned to the same assignee as this application and whose disclosure is incorporated by reference herein.

FIELD OF INVENTION

This invention relates to a novel process of resolving (R,S)-1-(3-hydroxyphenyl)-2-methylamino ethanol.

INTRODUCTION AND BACKGROUND OF THE INVENTION

The title compound was discovered as a useful synthetic adrenergic drug with many applications because of its vasoconstricting activity. For a number of years 'phenylephrine' was used as its racemic mixture including some of its pro-drugs (see: Legerlotz, U.S. Pat. No. 1,932,347; Hussain et al, U.S. Pat. No. 3,825,583; Bodor et al, U.S. Pat. No. 4,028,368 and U.S. Pat. No. 4,158,005). Although recognized as the more active form the levorotatory isomer (R)-phenylephrine was marketed only much later. It was also assumed that the racemic phenylephrine undergoes racemization in presence of acids in the gastric chamber like some of the catecholamines and pseudoephedrine. However, Legerlotz (see: DE 585164 C) had reported that high pressure heating with hydrochloric acid for a number of hours was required to inactivate 'active' phenylephrine, leading mostly to a small fraction of the substance to its racemic mixture and to other unidentified substances. In a series of articles in *J. Pharmacol. Exptl. Therap.*, from 1967 to 1972 with the general title "*Steric aspects of adrenergic drugs*", Patil et al have demonstrated the superiority of dextro-isomers over the levo-isomers of several sympathomimetic phenylethyl amines, including l-phenylephrine or (R)-phenylephrine (Formula 2). Several methods of synthesizing the molecule of Formula 1 below have been reported in literature leading to the formation of the racemic mixture. There is no published method of resolution of the racemic mixture of the molecule into its l-isomer and its isolation. Legerlotz has described (DE 543529) a method of resolving 1-(2-hydroxyphenyl)-2-methylamino ethanol and 1-(4-hydroxyphenyl)-2-methylamino ethanol with resolving agents like (+)-tartaric acid, d-camphorsulfonic acid and l-bromocamphorsulfonic acid. However, the undesired d-isomers of the amino alcohols only crystallized, the required isomers remaining in the mother liquors. A tedious work up is needed to recover the desired amino alcohol from the mother liquor. The yields of the isomers are not given. The specific rotation of the recovered undesired isomer is recorded but not that of the desired l-isomers. No procedure is given for the recovery of the desired isomer from the mother liquor. More to the point, it is to be noted that no example for the corresponding 3-hydroxyphenyl analog, the subject of this application, is described.

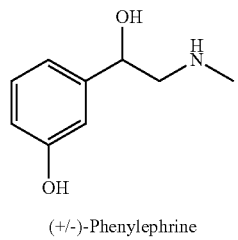

(+/-)-Phenylephrine

Formula 1

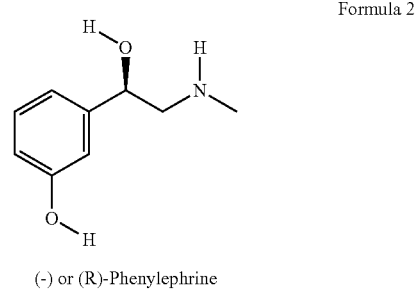

(-) or (R)-Phenylephrine

Formula 2

However, there are several asymmetric methods of synthesis reported for obtaining the R-isomer. These make use of the prochiral ketone precursor (Formula 3) for asymmetric reduction (hydrogenation) with catalysts containing transition metals like ruthenium, rhodium and iridium more frequently, along with complex chiral ligands. (see: IN 221620, U.S. Pat. No. 6,187,956, WO 2008 077560, WO 2009 086283, Takeda et al, *Tetrahedron Letters*, 1989, 30 367-370). In most of these processes the phenolic group or the secondary amino group or both, are protected and later deprotected. Recently reduction of α-haloketone (Formula 4) without protection of the phenolic group has been achieved using a microbial alcohol dehydrogenase enzyme from *Aromatoleum aromaticum* or *Azoarcus* sp. (See: WO 2010 031776). In this process the methylamino group is introduced last, i.e. after resolution.

Gurjar et. al. have described another approach by kinetic resolution of a racemic styrene oxide (Formula 5) in presence of a complex ligand followed by isolation of the required isomer and reaction with methylamine to give (R)-phenylephrine, (*Org. Proc. Res. Dev.*, 1998, 2, 422-424). The starting material is 3-hydroxy benzaldehyde which is more expensive than the usual 3-hydroxy acetophenone. Besides there is necessity of protecting the phenolic group and deprotecting it at later stage and use of an expensive complex chiral ligand. All these methods suffer from expensive chiral ligands and metallic catalysts, high pressure hydrogenations, etc. Thus there is a need for an efficient method of separation of the optical isomers of phenylephrine and a viable recovery of the required (R)-phenylephrine.

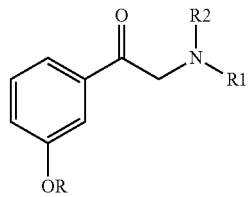

Formula 3

-continued

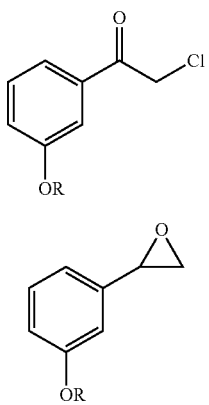

Formula 4

Formula 5

OBJECTIVES OF THE INVENTION

One exemplary objective of this invention was to find a suitable resolving agent for an efficient resolution of the racemic mixture of 1-(3-hydroxyphenyl)-2-methylamino ethanol or (R,S)-phenylephrine.

Another exemplary objective was to completely remove the resolving agent after resolution step such that the final drug substance is free from even traces of the resolving agent.

Yet another exemplary objective was to also remove the unwanted isomer of phenylephrine to such an extent that the desired isomer is substantially free from it.

A desired exemplary objective was recovery of the resolving agent of sufficient purity for reuse in next batch process for same purpose. Another desired objective was recovery of the unwanted isomer of the drug substance for possible conversion to the required isomer by chemical or physicochemical processes.

SUMMARY OF THE INVENTION

It has been possible to resolve racemic mixture of 1-(3-hydroxyphenyl)-2-methylamino ethanol using (R)-naproxen efficiently. The resolving agent could be recovered in good yields and purity besides the required isomer. The recovered resolving agent could be reused in the next batch of resolution step. The unwanted isomer could be recovered in good yield and purity suitable for recycling for value addition.

DETAILED DESCRIPTION OF THE INVENTION

We evaluated several commonly used chiral resolving acids like d-tartaric acid, l-pyroglutamic acid, l-lactic acid, l-mandelic acid etc. None proved satisfactory as can be seen from the Table 1 below.

As one of the major manufacturers of S-naproxen, we have access to both S-naproxen and R-naproxen in large quantities. The S-naproxen did form a salt with racemic phenylephrine, which was recovered as a solid material. On liberating the base from the salt, it was found that the undesired S-isomer of phenylephrine had crystallized with low enantiomeric purity and yield. We then tried the available R-naproxen for resolving racemic phenylephrine. Surprisingly we found that it formed a salt with R-phenylephrine efficiently and its solubility differed from that of its isomeric compound. We now report successful adoption of this technique to resolution of racemic phenylephrine and recovery of R-phenylephrine both in the laboratory and on a commercial scale. R-Naproxen has also been successfully utilized as a resolving agent for an intermediate in the preparation of sertraline (Hari Babu et. al, IN 216663) reported from this laboratory.

Racemic phenylephrine may be prepared by any of the reported methods, for example U.S. Pat. No. 1,932,347. In our process it was obtained by reduction of the ketone of formula 3, in which R=H, R1=$CH_3$ and R2=$CH_2C_6H_5$ followed by removal of the benzyl group to form compound of formula 1, similar to procedure outlined by Sergievskaya and Ravdel, *J. Gen. Chem. USSR,* 22, 1952, 559-563 (in English translation). To a solution of R-naproxen in methanol a hot solution of racemic compound of formula 1 in methanol is added and stirred for some time to induce formation of salt of R-naproxen with R-phenylephrine. On cooling the reaction mixture, the salt crystallizes out. The salt is then filtered and washed with cold methanol to remove undesired substances including the S-phenylephrine if any, salt of R-naproxen with S-phenylephrine and excess R-naproxen, all of which are soluble in methanol. The methanolic filtrate is reserved for recovery of these substances. The isolated salt R-phenylephrine-R-naproxen is suspended in water and then treated with aqueous alkali until a clear solution is obtained. To this hydrochloric acid is added drop wise to initiate breaking the salt and precipitation of R-naproxen. R-phenylephrine hydrochloride salt formed at the same time remains in solution. The precipitated R-naproxen is filtered, washed with water and dried for reuse as a resolving agent in the next batch. The aqueous solution containing R-phenylephrine hydrochloride can be subjected to direct recovery or further purification by liberating free base, extraction into organic solvent, crystallization and conversion to hydrochloride or other pharmaceutically acceptable salts.

One skilled in the art can improvise modifications to the above procedure in several aspects. For example it is possible to use the racemic phenylephrine hydrochloride salt, suspend it in methanol and add the requisite amount of alkali to liberate the free base before adding the R-naproxen to it. Phenylephrine base is not soluble in water but may be rendered

TABLE 1

| | | | Optical rotation for HCl salt | | |
| --- | --- | --- | --- | --- | --- |
| S. No | Resolving agent | Salt formation | Standard | Obtained | Remarks |
| 1 | (+)-Tartaric acid | Salt formed | $[\alpha]_D = -42$ to $-47.5°$ | $[\alpha]_D = +15.6°$ | Isolated compound shows positive rotation. |
| 2 | (−)-Pyroglutamic acid | Salt not formed | $[\alpha]_D = -42$ to $-47.5°$ | — | No resolution |
| 3 | (S)-(+)-Lactic acid | Salt not formed | $[\alpha]_D = -42$ to $-47.5°$ | — | No resolution |
| 4 | (R)-(−)-Mandelic acid | Salt not formed | $[\alpha]_D = -42$ to $-47.5°$ | — | No resolution |
| 5 | (S)-Naproxen | Salt formed | $[\alpha]_D = -42$ to $-47.5°$ | $[\alpha]_D + 34.0°$ | Isolated compound shows positive rotation. | soluble at a temperature above 80° and higher dilution but at lower dilution in hot methanol. Suitable combination of solvent, dilution and temperature may be chosen depending on the size of input. (See Table 2 below). R-naproxen may be added as a solution in methanol or as a solid to keep a low solvent ratio enabling better recovery of the salt.

TABLE 2

| | | | Solubility | | |
|---|---|---|---|---|---|
| S. No. | Solvent | Temp (° C.) | 1 g in 10 mL | 1 g in 30 mL | 1 g in 100 mL |
| 1 | Water | 25-30° C. | Not soluble | Not soluble | Not soluble |
| 2 | | 60-80° C. | Not soluble | Not soluble | Soluble |
| 3 | | 100° C. | Not soluble | Soluble | Soluble |
| 4 | Methanol | 25-30° C. | Not soluble | Not soluble | Soluble |
| 5 | | 60-80° C. | Not soluble | Soluble | Soluble |

The R-phenylephrine-R-naproxen salt can be suspended in water and hydrochloric acid added to it, which results in breaking the salt and precipitating the R-naproxen while retaining in solution the R-phenylephrine hydrochloride formed. The acid used for breaking the salt can be any mineral acid although hydrochloric acid is convenient to handle. The resolving agent R-naproxen can be recovered by filtration or also by extraction with an organic solvent like toluene.

The S-phenylephrine-R-naproxen salt can be similarly processed to recover the R-naproxen and S-phenylephrine. Methods are described in literature for conversion of the S-phenylephrine to R-phenylephrine via oxidation to corresponding ketone or by racemisation or inversion for value addition.

The resolving agent R-naproxen forms salts with both the R- and S-isomers of phenylephrine. For this reason the amount of R-naproxen required is equal to 1:1 in molar ratio. The two salts surprisingly exhibit different solubilities in water and methanol. Advantage is taken of this property in this novel process. If the R-naproxen input is reduced, the recovery of the R-phenylephrine-R-naproxen salt is correspondingly reduced and unreacted racemic phenylephrine remains in the reaction mixture. In place of methanol another suitable solvent like ethanol or isopropanol or acetone may be used.

It was also noted that a high optical purity of the R-naproxen was not needed for efficient resolution. Theoretically the R-naproxen of OR −64° is pure and should yield best results. Initially R-naproxen of OR −61.9° was used with good results. During further experimentation it was surprisingly found that R-naproxen of OR about −50° was adequate to get optimum salt formation. In fact the yield and recovery was lower when R-naproxen of higher purity was employed although the optical purity of the recovered salt was as good. It was also found that R-naproxen of OR less than about −45° was not desirable as it resulted in lower purity of the recovered salt. (Tables 3 &4)

TABLE 4

| | R-Naproxen Input | | Recovered R-Naproxen | | | Assay % |
|---|---|---|---|---|---|---|
| S. No. | Qty. (g) | OR° | Output (g) | Yield % | OR° | (Titrimetric) |
| 1 | 78 | (−)50 | 33 | 42.3 | (−)52.6 | 100.5 |
| 2 | 78 | (−)50 | 33 | 44.8 | (−)53.5 | 98.4 |
| 3 | 78 | (−)50 | 35 | 44.8 | (−)55.5 | 100.4 |
| 4 | 113 | (−)50 | 62 | 54.8 | (−)55.5 | 100.0 |
| 5 | 113 | (−)50 | 50 | 54.2 | (−)53.5 | 98.8 |
| 6 | 113 | (−)50 | 58 | 51.6 | (−)52.6 | 99.3 |

It is to be noted that R-naproxen is an inactive isomer of the S-naproxen and is thus harmless. Because it is practically insoluble in acidic media whereas the phenylephrine hydrochloride is completely soluble in acidic media, total separation and elimination of the resolving agent is achieved. In all the batches of the R-phenylephrine hydrochloride prepared by this process we could not detect even traces of R-naproxen.

The following examples are illustrative of the invention and achieved objectives but are not limited to the details provided. One skilled in the art can easily modify the details to suit the inputs and desired outcomes.

EXAMPLES

Example 1

(a) To 385 mL of methanol 27.7 g of R-naproxen (OR −61.9° c.=1 in chloroform) are added and stirred at ambient temperature until a clear solution is obtained. A solution of 20 g of racemic phenylephrine base is separately prepared in 195 mL of methanol by warming to about 65° C. When a clear solution is obtained this solution is rapidly added to the solution of naproxen. The mixture is stirred while slowly cooling to ambient temperature for a period of about 2 hours to complete salt formation. The mixture is then filtered through a sintered glass funnel or Buchner filter assembly with mild vacuum. The solid filter is washed with about 13 mL of methanol once. The filtrate is collected and reserved for recovery of the salt S-phenylephrine-R-naproxen and excess (unreacted) resolving agent. The isolated solid salt is dried in a vacuum oven at ambient temperature for two hours. Yield of practically dry off white crystalline solid was 18.6 g, i.e. 39.1% based on theoretical yield of the salt from input racemic base expected to contain 50% as required isomer. M.r. of salt: 193-196° C.

(b) A slurry of 12 g of the salt obtained as in (a) above is prepared in about 50 mL of water at ambient temperature. About 25 mL of a 10% aqueous solution of sodium hydroxide is added drop wise while stirring until a clear solution is obtained. The pH of the solution may be around 13. This ensures complete breaking of the salt, converting all the R-naproxen into its sodium salt. Now about 8.5 ml of hydro-

TABLE 3

| DL-Phe HCl Input (g) | Assay/ HPLC A % | R-Nap Input (g) | R-Nap OR | Mol. Eq. Phe:Nap | Salt Yield (g) | L-Phe Base Yield (g) (%) | Base OR | Assay/ HPLC A % |
|---|---|---|---|---|---|---|---|---|
| 100 | 98.5 | 78.0 | (−)50.0 | 1.0:0.69 | 108.0 | 32.0 (73.0) | (−)30.6 | 99.1 |
| 100 | 98.5 | 91.1 | (−)62.0 | 1.0:0.79 | 124.5 | 37.7 (86.1) | (−)32.2 | 99.4 |
| 100 | 98.5 | 98.2 | (−)57.5 | 1.0:0.87 | 121.5 | 39.5 (90.2) | (−)33.6 | 99.6 |
| 100 | 98.5 | 113.0 | (−)50.0 | 1.0:1.0 | 129.0 | 38.3 (87.4) | (−)32.9 | 99.4 |
| 100 | 98.5 | 137.8 | (−)41.0 | 1.0:1.2 | 126.5 | 38.1 (87.0) | (−)32.5 | 99.4 | chloric acid is added drop wise. First any excess of sodium hydroxide gets neutralized followed by decomposition of the sodium naproxen to free R-naproxen and sodium chloride. Insoluble R-naproxen precipitates. To complete the precipitation, the pH is adjusted to about 1 to 1.5 and stirred for about 15 minutes. The mixture is filtered suitably and the solid washed with water. The recovered solid R-naproxen is dried in vacuum oven at about 40° C. Yield 6.2 g (of OR −55.6°, c=1 in $CHCl_3$; ~35% of input; remaining to be recovered from the salt with the other isomer). The filtrate containing R-phenylephrine hydrochloride salt is concentrated suitably (distillation under reduced pressure at <50° C. to about three fourth of its volume) and treated with a 20% solution of ammonia to neutralize the hydrochloride salt for liberating free R-phenylephrine base. To hasten material formation sides of the container are scratched and cooled. The solid so obtained is filtered, washed with a little acetone and dried in vacuum oven at about 40° C. Yield 3.8 g (~29.5%), m.p. 169-172° C.

(c) The free base (3.8 g) obtained as above was suspended in about 6 mL of methanol and a methanolic solution of hydrochloric acid containing a calculated amount of the acid. A clear solution is formed. On distilling off the methanol in a rotary evaporator under reduced pressure at <40° C., a solid residue is obtained, which is then treated with 2-propanol to dissolve the solid followed by addition of diisopropyl ether to induce crystallization of the R-phenylephrine hydrochloride. Yield 4.5 g (~28.7% calculated on input of racemic phenylephrine base); M.r. 129-133° C.; OR −42.3; HPLC purity 99.5% (A); Assay 101.8% (titrimetric).

(d) The filtrate from step (a) above is subjected to distillation at <50° C. The crude residue is treated with 25 mL water followed by 30 mL of a 10% solution of sodium hydroxide to obtain a clear solution. The solution is then acidified with HCl until a pH of <2 is achieved. The precipitated R-naproxen is filtered off and dried in vacuum oven at ~40° C. for two hours. Yield 18.0 g (65% of OR −33.4°, c=1 in $CHCl_3$). Together with R-naproxen already recovered under step (b) above, this amounts to practically quantitative recovery of the resolving agent.

(e) The filtrate from step (d) above after precipitation of R-naproxen, is concentrated to about three-fourth of its volume at about 50° C. under reduced pressure. Then about 90 mL of a 20% solution of ammonia is added to a final pH of 9. On scratching the sides of the container while cooling to about 5° C., S-phenylephrine base crystallizes out which is collected and dried in vacuum oven at about 40° C. for about two hours. Yield 7.5 g (37.6%), m.p. 148-152° C., OR +32.3°.

Example 2

(a) Racemic phenylephrine hydrochloride (50.0 g, 0.2457 moles) was suspended in 450 mL of methanol to which solid sodium hydroxide (9.8 g, 0.2457 moles) was added and the reaction mixture was stirred for 30 minutes at ambient temp. To the reaction mass solid R-naproxen (56.5 g, 0.2457 moles, OR −50°) was added. The reaction mixture was warmed to 50-60° C., and then stirred for 1 hr at 50-60° C. The suspension was cooled to 25-29° C. and stirred for 30 minutes to obtain crystalline phenylephrine-R-naproxen salt. The salt was filtered and washed with 25 ml of methanol. The wet salt weighed ~62.5 g (moisture content <0.75%). The filtrate and washings were combined and reserved for recovery of S-phenylephrine and R-naproxen.

(b) The phenylephrine-R-naproxen salt (62.5 g) was suspended in 75 mL of purified water, pH adjusted to <2 with HCl (~12 mL) at 25-35° C. and charged with 208 mL of toluene. The suspension was warmed to 75-80° C. and maintained for 30 minutes. The reaction mass separated into two layers. The upper toluene layer separated and the bottom aqueous layer was extracted with 55 mL of toluene at 75-85° C. The toluene extracts were combined and reserved for recovery of R-naproxen. The aqueous layer was cooled to about 15° C. and the pH adjusted to about 9 with ammonium hydroxide solution (~20 mL). The reaction mixture was further cooled to 1-5° C. and stirred for about 1 hr at 1 to 5° C. The crystalline R-phenylephrine base obtained was filtered, washed with 25 mL of purified water and dried under vacuum at 75° C. until moisture content was <0.2%. Yield 18.4 g (90%), m.r.: 170-180° C., OR: −30 to −35° (c=2% in MeOH).

(c) The R-phenylephrine base (18.4 g, 0.11 moles) was suspended in 74 mL of isopropanol (IPA), IPA-HCl added until acidic and stirred for 30 minutes at 55-65° C. After cooling to room temperature, the precipitated R-phenylephrine hydrochloride salt was filtered and washed with IPA. It was further purified by treatment with a mixture of hot methanol and IPA, cooling to 0-5° C. and filtering the pure R-phenylephrine HCl. Yield 19.0 g (84.5%), melting range 140-145° C., OR −42° to −47.5°, (c=5% in $H_2O$).

(d) The reserved toluene layer from step (b) above was cooled to 5° C. and stirred for 15 minutes. The crystalline precipitate of R-naproxen was filtered and dried for about 2 hrs at 80° C. (moisture content <0.15%). Yield 27.8 g (49.2%), OR −55.5°, (c=1% in MeOH), assay 99.15%.

(e) The methanolic filtrate obtained in step (a) above, about 500 mL, was concentrated under reduced pressure at less than 50° C. To the thick residue about 70 mL water and 170 mL toluene are added followed by HCl (about 13 mL) to adjust the pH of the aqueous layer to about 2. The mixture is stirred and warmed to about 75-85° C. for about 30 minutes. On stopping stirring, the mixture separates into two layers. The lower aqueous layer is collected and extracted with toluene, the two toluene layers combined and reserved for recovery of R-naproxen. The aqueous layer containing hydrochloride of S-phenylephrine was cooled to 1-5° C. and treated with ammonia solution (about 18 mL) to a pH>9 and stirred to complete precipitation of S-phenylephrine base. The fine crystalline base is filtered, washed with a little water and dried at <55° C. in a vacuum oven (moisture content <0.3%). Yield 19.4 g (94.9%), melting range 170 to 172° C., OR +25 to 30° (c=2% in MeOH).

(f) The filtrate from step (e) above containing R-naproxen was concentrated, stirred for a few minutes and cooled to about 5° C. The crystallized R-naproxen was filtered and dried under reduced pressure at <80° C. (moisture content <0.15%). Yield 28.5 g (50.4%), OR −46.3 (c=1% in MeOH), assay 99.6%.

Example 3

(a) Racemic phenylephrine hydrochloride (360 kg, assay 99.5%) is charged into the reactor and stirred for not less than 30 minutes at 25-35° C. Caustic soda flakes (71 kg) are charged into reactor and stirred for 30 minutes. The resolving agent (R)-naproxen (407 kg of OR −50°) is charged and the temperature is raised to 50-60° C., maintained for not less than 1 hour at 50-60° C., gradually cooled to 25-29° C., maintained for another 30 minutes and filtered. The wet cake of R-phenylephrine-R-naproxen salt is washed with 150 L of methanol. Yield ~450 kg (wet).

(b) The salt from step (a) above (900 kg) charged into a reactor containing 1080 L of purified water and the pH is adjusted to <2 with HCl at 25 to 35° C. Then 3800 L of toluene is charged to the mass and the liberated resolving agent is extracted into toluene at 75 to 85° C., separated and reserved for its recovery. The aqueous layer is cooled to 20 to 30° C., charged into a reactor, pH is adjusted to between 9 and 10 with liquor ammonia at 10 to 20° C., the mass is further cooled to 1 to 5° C., maintained for about an hour and filtered. The wet (R)-phenylephrine base is dried (moisture content <0.2%). Yield 265 kg (90%), OR −32.3°, assay 99.89%.

(c) Dry (R)-phenylephrine base (300 Kg) is charged into reactor containing 1200 L of isopropanol and pH is adjusted to less than 1 with IPA-HCl at 20 to 30° C. Then the temperature is raised to 55 to 65° C. The mass is gradually cooled and maintained for not less than 2 hours at −1 to 5° C. The product is filtered and the cake is washed with 60 L of isopropanol. The wet cake of (R)-phenylephrine hydrochloride is purified and dried. Yield 310 kg (84.8%), assay 99.9%, OR −44.79° (c=5% in water).

Without further elaboration the foregoing will so fully illustrate our invention that others may, by applying current or future knowledge, adopt the same for use under various conditions of service.

We claim:

1. A process for resolution of racemic 1-(3-hydroxyphenyl)-2-methylamino ethanol to obtain (R)-1-(3-hydroxyphenyl)-2-methylamino ethanol, (R-phenylephrine) comprising the steps of:
   (a) treating racemic 1-(3-hydroxyphenyl)-2-methylamino ethanol or its salt with (R)-2-(6-methoxy-2-naphthyl) propionic acid, (R-naproxen) or its salt, in a suitable medium as a solution or suspension to precipitate a first salt of (R)-1-(3-hydroxyphenyl)-2-methylamino ethanol with R-naproxen;
   (b) filtering the precipitated first salt, optionally washing and drying the first salt and recovering the first salt;
   (c) treating the recovered first salt with an adequate amount of an acid to liberate free R-naproxen and converting the R-phenylephrine to a second salt of the acid added;
   (d) treating a solution of the second salt of R-phenylephrine as obtained in step (c) with a base to liberate free R-phenylephrine base, optionally washing and drying the precipitated solid; and
   (e) converting the free R-phenylephrine base to a pharmaceutically acceptable salt.

2. A process according to claim 1 (a) in which the suitable medium is formed by using water and methanol or mixtures thereof, with addition of alkali if needed, to obtain a solution or suspension by adjusting the temperature as necessary.

3. A process according to claim 1 (c) in which the added acid is a mineral acid.

4. A process according to claim 1 (c) in which the liberated free R-naproxen is recovered by filtration, washing and drying or by extraction with a solvent and suitable work up.

5. A process according to claim 1 (d) in which the base is an inorganic base from the group consisting of sodium hydroxide, sodium carbonate, sodium bicarbonate, potassium hydroxide and potassium carbonate.

6. A process according to claim 1 (b) in which the filtrate is concentrated to allow recovery of R-naproxen as a solid salt of (S)-1-(3-hydroxyphenyl)-2-methylamino ethanol, and optionally washed, dried and purified.

7. A process according to claim 6 in which the salt is decomposed by treatment with a mineral acid, preferably hydrochloric acid, to obtain R-naproxen as a solid and the second salt of (S)-1-(3-hydroxyphenyl)-2-methylamino ethanol with the mineral acid used remaining in solution, filtering the R-naproxen, washing, drying and purifying, if necessary.

8. A process in which the filtrate obtained in claim 7 containing (S)-1-(3-hydroxyphenyl)-2-methylamino ethanol as a second salt is concentrated and/or treated with an inorganic base to liberate free (S)-1-(3-hydroxyphenyl)-2-methylamino ethanol base as a solid and filtering, washing and drying as necessary.

9. A process according to claim 7 in which the recovered R-naproxen is reused as a resolving agent in another batch of the resolution process according to claim 1.

10. A process according to claim 3 in which the mineral acid is hydrochloric acid.

11. A process according to claim 4 in which the solvent is toluene.

* * * * *